United States Patent [19]
Borho et al.

[11] Patent Number: 5,814,231
[45] Date of Patent: Sep. 29, 1998

[54] SEPARATION OF LIQUID EUTECTIC MIXTURES BY CRYSTALLIZATION ON COLD SURFACES AND APPARATUS FOR THIS PURPOSE

[75] Inventors: Klaus Borho, Mutterstadt; Jörg Heilek, Bammental; Gunter Schnabel, Fussgönheim, all of Germany

[73] Assignee: BASF Aktiengesellschaft, Ludwigshafen, Germany

[21] Appl. No.: 711,017

[22] Filed: Sep. 9, 1996

[30] Foreign Application Priority Data

Oct. 2, 1995 [DE] Germany .................. 195 36 827.4

[51] Int. Cl.$^6$ .................................................. C30B 21/00
[52] U.S. Cl. .................. 210/737; 210/774; 23/295 R; 23/301; 62/532
[58] Field of Search ................... 210/710, 737, 210/773, 774; 23/295 R, 301; 62/532

[56] References Cited

U.S. PATENT DOCUMENTS

| | | | |
|---|---|---|---|
| Re. 32,241 | 9/1986 | Saxer | 62/542 |
| 2,983,757 | 5/1961 | Zaugg | 260/570 |
| 3,607,115 | 9/1971 | Bleil | 23/301 |
| 3,607,141 | 9/1971 | Montagna et al. | 23/301 |
| 3,621,664 | 11/1971 | Saxer | 62/58 |
| 4,025,573 | 5/1977 | Hathway | 62/532 |
| 4,529,444 | 7/1985 | Björling et al. | 62/532 |
| 4,632,809 | 12/1986 | Otto et al. | 422/254 |
| 4,654,064 | 3/1987 | Cheng et al. | 62/532 |
| 4,795,571 | 1/1989 | Holzknecht et al. | 210/774 |
| 5,434,316 | 7/1995 | Kissinger | 568/724 |

FOREIGN PATENT DOCUMENTS

| | | |
|---|---|---|
| 451597 | 10/1948 | Canada . |
| 3708709 | 3/1987 | Germany . |
| 9002627 | 2/1979 | Japan . |
| 460 834 | 2/1937 | United Kingdom . |
| 1273278 | 5/1972 | United Kingdom . |

Primary Examiner—Jay H. Woo
Assistant Examiner—Betsey J. Morrison
Attorney, Agent, or Firm—Keil & Weinkauf

[57] ABSTRACT

A process for separating a liquid eutectic mixture by crystallization of one eutectic forming substance of the mixture on a cold surface to which seed crystals of the eutectic forming substance have been applied in the form of a seed crystal layer, and subsequent removal of the eutectic forming substance in liquid form after heating of the surface.

8 Claims, 1 Drawing Sheet

SEPARATION OF LIQUID EUTECTIC MIXTURES BY CRYSTALLIZATION ON COLD SURFACES AND APPARATUS FOR THIS PURPOSE

The present invention relates to a process and an apparatus for separating liquid eutectic mixtures by crystallization on cold surfaces to which seed crystals are applied in the form of a seed crystal layer on which grow eutectic formers of the same type, which are removed in liquid form after heating of the surfaces.

The separation of substances by crystallization is of particular interest when enantiomer mixtures, i.e. mixtures of optically active isomers, are to be separated. In these cases, other thermoseparation methods (extraction, distillation) have no selectivity; in these methods, a separation effect can be achieved only by the use of expensive assistants (chiral substances).

As a rule, it is necessary to separate substances with a very high yield, based on the desired product. This is an essential problem of crystallization as a separation method, since in most cases the desired substance and undesirable secondary components form eutectic mixtures which cannot be further separated without special measures. Accordingly, lower yields of desired substance are obtained in these cases, depending on the eutectic compositions. In the case of racemic enantiomer mixtures in which the racemate is at the same time the eutectic mixture (racemic conglomerate), no separation of substances is possible without special measures, even by means of crystallization.

Crystallization has therefore been used as a separation method also for separating eutectic compositions. It is known that eutectic mixtures can be separated by initially taking individual seed crystals of the eutectic-forming substances (also referred to below as EF=eutectic formers) in melts or solutions having a eutectic composition (referred to below as eutectic liquid), allowing the seed crystals to continue growing under defined conditions with regard to supersaturation (within the metastable range) by selective growing of the EF on the seed crystals of the same type and separating off the individual crystals substantially in pure form from the melt or solution after growth by suitable measures.

In known crystallization processes and apparatuses for separating eutectic mixtures, in particular for separating enantiomers, the EF are crystallized separately either selectively in two coupled crystallizers (German Patents 1,807, 495 and 2,109,456) or in a common crystallizer (U.S. Pat. No. 2,983,757). The common feature of all processes/apparatuses described is that the eutectic liquids are seeded with individual crystals of the EF in order to be able selectively to crystallize the EF.

As a result of introducing individual seed crystals into the eutectic liquid, it is inevitable that the EF are obtained either as disperse crystalline masses in a suspension (crystal slurry) or in special apparatuses as individual crystals in defined three-dimensional arrangements.

The suspended crystals therefore have to be separated from the eutectic liquid by a method which is difficult and technically complicated (for example by means of centrifuges, filters and gravity separators), especially in the case of melt systems, or the requirement for a defined three-dimensional arrangement necessitates complicated introduction of the individual seed crystals into the crystallizer and collection of the grown crystals in a procedure which is just as complicated.

A further disadvantage of the known processes/apparatuses is that, in order to seed the eutectic liquid, the seed crystals must be handled in the form of a slurry or as bulk material.

The above mentioned disadvantages have meant that the processes/apparatuses described cannot be used on a large industrial scale.

It is an object of the present invention to provide a process and an apparatus for separating eutectic liquid mixtures, which process and which apparatus avoid these disadvantages and can be used in a simple and reliable manner on a large industrial scale.

We have found that this object is achieved, according to the invention, by a process for separating a liquid eutectic mixture by crystallization of one eutectic-forming substance of the mixture on a cold surface to which seed crystals of the eutectic-forming substance have been applied in the form of a seed crystal layer, and subsequent removal of the eutectic-forming substance in liquid form after heating of the surface.

In an advantageous development of the invention, the seed crystal layer is formed on the cold surface by a method in which the cold surface is brought into contact with a pure melt, solution or suspension of the eutectic-forming substance and the corresponding seed crystal layer is formed by cooling, and in which the cold surface is then brought into contact with the eutectic mixture to be separated. In order to form the seed crystal layers, the pure melt, solution or suspension of at least one eutectic-forming substance is used, two pure melts, solutions or suspensions of two eutectic-forming substances preferably being used for forming seed crystal layers on two separate layers which are then brought into contact with the eutectic mixture to be separated. The terms pure melts, solutions or suspensions or pure EF melts include, according to the invention, not only melts, solutions or suspensions of pure substances in the conventional sense but all melts, solutions or suspensions of mixtures which, with respect to the EF, are purer than the eutectic mixture to be separated.

In a further embodiment of the invention, the eutectic mixture is circulated during growing of the crystal layers on the cold surfaces, and, after the growth of the crystal layers, the circulation is terminated and the residual eutectic liquid is removed.

A wash or sweating step can then be carried out. During the washing, the crystal layers grown on the cold surfaces are brought into contact with a wash liquid and are separated from the latter again. As a result, the residual eutectic liquid remaining on the crystal layers is replaced by the wash liquid, which is preferably purer. In particular, a relatively long residence time of the wash liquid on the crystal layers also results in exchange of impurities between the purer wash liquid and less pure parts of the crystal layers by diffusion. Fresh eutectic mixture or pure EF melt is preferably used as the wash liquid. During sweating, the temperature of the crystal layer is increased, after removal of the residual eutectic liquid, to a value which is between the melting points of the eutectic mixture and of the pure EF substance. This results in partial melting of less pure parts of the crystal layer.

The crystal layers are then liquefied by heating, and the liquids are removed separately.

After the one or more eutectic-forming substances have been removed, a crystal layer of only one eutectic-forming substance is formed again on a cold surface by bringing the cold surface into contact with a pure melt, solution or suspension of a eutectic-forming substance and feeding the eutectic mixture to the cold surface again after formation of a seed crystal layer.

The cold surfaces used may be flat or cylindrical cold surfaces, for example pipes. These cold surfaces may be parts of a common heat exchanger, each of which parts is provided with a feed and a discharge.

The novel crystallization process operates, like all known processes/apparatuses, according to the fundamental principle of allowing the eutectic formers (EF) to grow in the metastable range on crystalline surfaces of the same type. In contrast to the known processes, however, the novel process is distinguished by the fact that the separation of the eutectic mixture is effected by crystallization on cold surfaces which are in contact with the eutectic liquid and on which at least one EF selectively grows as a layer or, preferably, two EF selectively grow as layers. In order to achieve selective growth of crystal layers, cold surfaces are first brought into contact, before the actual crystallization process, with the pure melt, solution or suspension of at least one EF, but preferably with the pure melts, solutions or suspensions of two EF, after which the pure melts, solutions or suspensions of the one or more, preferably of the two, EF are separated again from the cold surfaces and the thin liquid films remaining on the wet cold surfaces and comprising one EF, preferably two EF, are then partially or completely solidified to give seed crystal layers by reducing the temperature of the cold surfaces.

The application of a seed crystal layer to a cold surface by reduction of temperature can also be effected by solidifying the liquid film remaining on the cold surface after melting of the crystal layer from the preceding cycle. The cold surfaces provided with seed crystal layers are then brought into contact with eutectic liquid, and at least one EF, preferably two EF, is or are then allowed to grow selectively to thicker crystal layers on the cold surfaces by temperature reduction.

If, in the novel process, only one EF is initially taken as a crystalline seed layer on the cold surfaces and allowed to grow as a layer, the second EF can either be introduced as in known processes by means of individual seed crystals and obtained as disperse crystals or obtained by spontaneous mass crystallization without seeding.

The cold surfaces which can be used in the novel process are not subject per se to any restriction and may be of any desired shape. Cylindrical cold surfaces, for example pipes, or flat cold surfaces are preferably used. The cold surfaces may be either completely immersed in eutectic liquid or in contact only with a trickle film of eutectic liquid, for example a pipe with flow through its full cross-section or a pipe through which a trickle film flows.

The solidification of a thin liquid film remaining on the cold surfaces was described in German Patents 1,769,123 and 3,708,709 for the introduction of a crystalline surface. There, however, the liquid film and hence also the resulting crystalline phase have the same composition on all cold surfaces. Moreover, the presence of a further crystalline phase is not envisaged or described. The possibility of the presence of two crystalline phases, preferably achieved by separating cold surfaces and providing them with seed crystal layers of different compositions, was not recognized. Furthermore, it was not recognized that the application of seed crystals in the form of a seed crystal layer on a cold surface can be used for separating eutectic mixtures.

If the EF are not obtained directly in sufficient purity by the novel process for separating eutectic mixtures, the pure EF melts obtained from the novel process can be further highly purified by known recrystallization methods.

According to the invention, the term eutectic former includes not only a single component of a eutectic mixture but may also include mixtures of two or more but not all eutectic-forming components of a eutectic mixture.

The process is suitable in general for separating all eutectic mixtures whose individual components are capable of forming crystals. The novel process is particularly advantageous for the separation of eutectic mixtures having melting points of the mixtures of from −30° to +200° C., preferably from 20° to 150° C. The separation of a eutectic mixture of the enantiomers R(+)-2-phenoxypropionic acid and S(−)-2-phenoxypropionic acid having an R/S composition of 96/4 and a melting point of 61° C. may be stated as an example. The crystallization temperature of the eutectic melt here is 61° C., so that the temperatures of the cold surfaces during crystallization are from 61° to about 30° C. A eutectic mixture of the enantiomers R(+)-2-(4-chloro-2-methylphenoxy)propionic acid and S(−)-2-(4-chloro-2-methylphenoxy) propionic acid having an R/S composition of 80/20 and a melting point of 79° C. may be stated as a further example. The crystallization temperature of the eutectic melt is 79° C., and the temperatures of cold surfaces during crystallization are therefore from 79° to about 40° C.

Eutectic mixtures of acrylic acid and its secondary components, as may form in the preparation of acrylic acid by oxidation of propane, can also be separated by the novel process, for example mixtures with acrylic acid, acetic acid, propionic acid, benzoic acid, allyl acrylate or furan-2aldehyde as EF. The eutectic mixture of the components of acrylic acid and acetic acid, composed of 55% of acrylic acid and 45% of acetic acid and having a melting point of −27° C., may be stated as an example of this.

The novel process is distinguished in general by simplicity and operational safety since there is no need to handle crystalline masses in solid form, i.e. no separation on filters or centrifuges and no solid transport processes are required. Especially as a process for separating eutectic mixtures, the particular advantage is that the complicated handling of the seed crystals in the form of a slurry or as bulk material is dispensed with. Instead, the initially introduced crystalline surface required for selective crystallization is realized in a very simple manner by applying a seed crystal layer to a cold surface, preferably by solidification of a liquid film on the cold surface.

Figure 1:
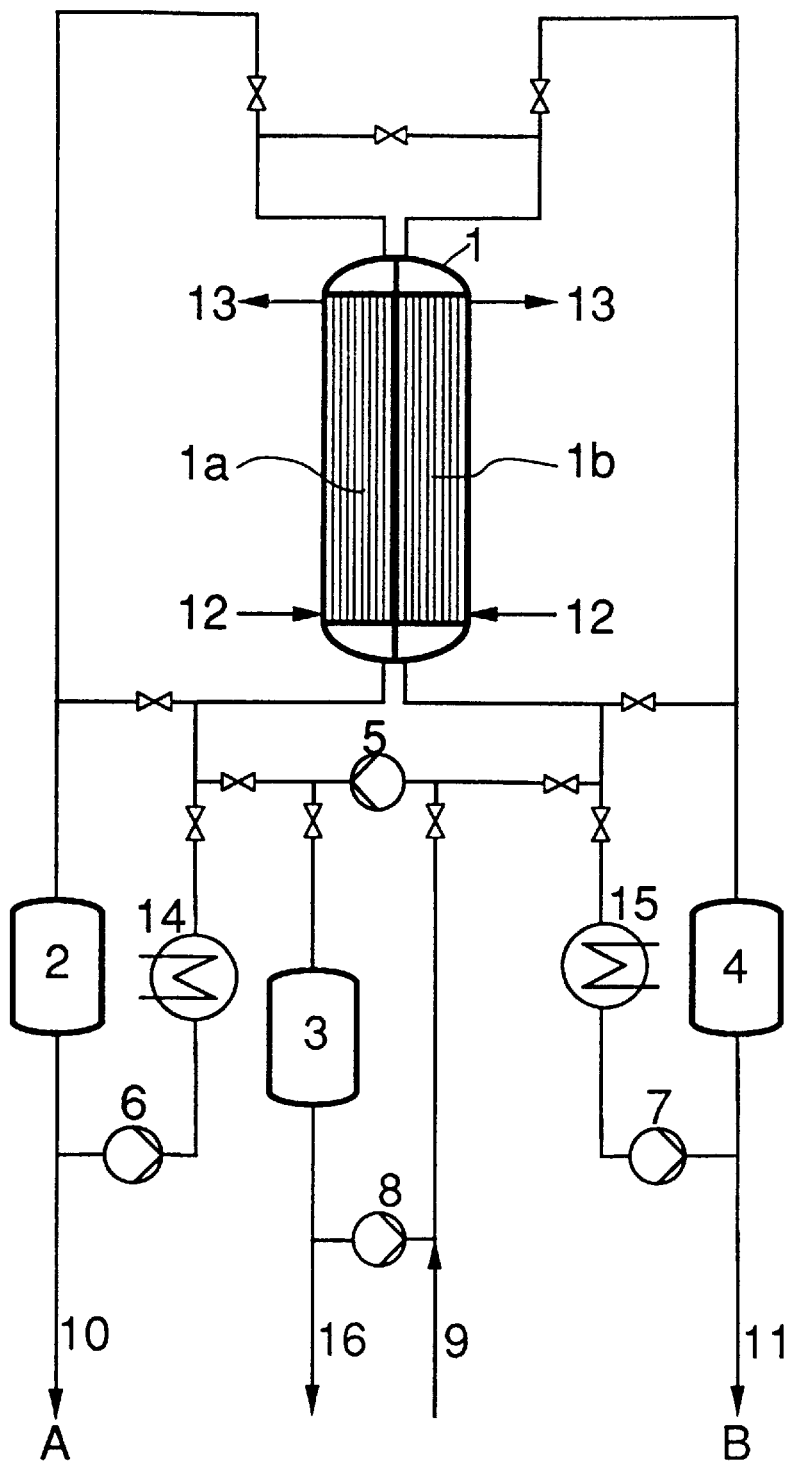
FIG. 1 is a schematic representation of an apparatus for carrying out the process of the present invention.

The invention also relates to an apparatus for carrying out the described process, wherein at least two heat exchangers (1a, 1b) provided with at least one feed pipe (12) and one discharge pipe (13) for a coolant are provided, the separate feed pipes of said heat exchangers being capable of being connected to a common feed pipe (9) and the discharge pipe of said heat exchangers being capable of being connected each to a separate collecting container (2, 4) or to a common collecting container (3). Preferably the heat exchanger (1) has flat or cylindrical cold surfaces. Preferably wherein the heat exchangers (1a, 1b) form a structural unit (1). Preferably the cold surface of the individual heat exchangers (1a, 1b) have different size or different proportions of the total cold surface.

Further details and advantages of the invention are described with reference to the example which is shown in the Figure and described below and which constitutes a preferred embodiment of the invention.

The crystallizer denoted by 1 in the Figure is divided structurally into the separate crystallization zones 1a and 1b. In the Example, this is a 2-pass tube-bundle heat exchanger. Three containers 2, 3 and 4 serve as collecting and feed volumes for the eutectic liquid and the pure melts of the EF. Four pumps 5, 6, 7 and 8 serve for transporting the liquids occurring in the system. Energy can be additionally fed to the system by means of heat exchangers 14 and 15, provided that this is not to take place exclusively via crystallizer 1.

The operational sequence of the process is as follows: Zones 1a and 1b of crystallizer 1 are first fed separately with one of the eutectic-forming substances (EF). In the present case, the substance denoted by EF A and taken from container 2 is fed to zone 1a, and the substance denoted by EF B and taken from container 4 is fed to zone 1b. The liquids are then discharged separately, A into container 2 and B into container 4. The cold surfaces are then cooled in order to solidify the liquid films remaining on the cold surfaces to give seed crystal layers. The cooling of the cold surfaces in the two zones of the heat exchanger serving as a crystallizer is effected by means of a coolant which is fed through the pipeline 12 and removed through the pipeline 13.

The eutectic liquid to be separated, with its components A and B, is then fed via feed pipe 9 into the crystallizer 1 and is circulated continuously by means of the pump 5 through the pipes of the crystallization zones 1a and 1b. The cold surfaces in the two zones of the crystallizer are cooled with the aid of the coolant fed in via the pipes 12 and removed via the pipes 13, so that the EF in the crystallization zones 1a and 1b grow selectively on the existing seed crystal layers and no new crystal nuclei form.

After a desired layer thickness has been reached, the cooling process is terminated, pump 5 is put out of operation and the residual eutectic liquid remaining in the crystallizer 1 is discharged into the container 3.

The crystalline layers adhering to the cold surfaces in the crystallization zones 1a and 1b are melted by increasing the temperatures of the cold surfaces to temperatures above the melting points of the EF. The melts A and B which flow away are collected separately in the containers 2 and 4 (A in container 2, B in container 4). In order to accelerate the melting process, pure melts of the EF may additionally be transported from the containers 2 and 4 by means of the pumps 6 and 7 and passed through the particular crystallization zones 1a and 1b. Energy for the melting process can additionally be supplied to the system by means of the heat-transfer media 14 and 15, unless this is to take place exclusively via the crystallizer 1.

After discharge of the pure EF melts from the crystallization zones 1a and 1b into the corresponding collecting containers 2 and 4, the residual films of the pure EF melts adhering in each case to the cold surfaces are frozen by reducing the temperatures of the cold surfaces in the crystallization zones and serve as seed crystal layers for the next crystallization cycle.

For filling the crystallizer again, fresh eutectic liquid is fed via pipe 9. The residual eutectic liquid present in container 3 can also be used for filling the crystallizer, via pump 8, or is completely or partially removed from the system via pipe 16.

The process described above is then repeated cyclically. When the containers 2 and 4 are sufficiently full, the particular pure melts A and B of the EF are removed from the system via the pipes 10 and 11.

If the pure EF substances have substantially different melting points or the composition of the eutectic mixture differs substantially from a ratio of 1:1, this can be taken into account when dividing the cold surfaces into zones. Where the melting points of the pure EF substances differ substantially (preferably in the case of temperature differences >10° C.), it may be useful to be able to heat and cool the EF-specific zones independently of one another. This is of interest in particular when freezing the seed crystal layers and melting the crystal layers. In the case of eutectic compositions which differ substantially from the ratio of 1:1 (preferably ratios of 60:40 and more unequal ones), a correspondingly larger cold surface can be provided for the proportionately predominant EF and a correspondingly smaller cold surface for the other EF. Different cold surface areas, numbers of cold surfaces and separate heating facilities can be achieved by segmenting a common heat exchanger or by using a plurality of different heat exchangers.

We claim:

1. A process for separating a liquid eutectic mixture, which process comprises crystallizing one eutectic-forming substance of the mixture on a cold surface to which seed crystals of the eutectic-forming substance have been previously applied as a seed crystal layer in the form of a solidified liquid film, and subsequently removing the eutectic-forming substance in liquid form after heating the surface.

2. A process as claimed in claim 1, wherein the seed crystal layer is formed on the cold surface by bringing the cold surface into contact with pure melt, solution or suspension of the eutectic-forming substance and the corresponding seed crystal layer is formed by cooling, and the cold surface is then brought into contact with the eutectic mixture to be separated.

3. A process as claimed in claim 1, wherein two pure melts, solutions or suspensions of two eutectic-forming substances are used for forming seed crystal layers on two separate cold surfaces which are then brought into contact with the eutectic mixture to be separated.

4. A process as claimed in claims 1, wherein the eutectic mixture is circulated during growing of the crystal layers on the cold surfaces, and, after the growth of the crystal layers, the circulation is terminated and the residual eutectic liquid is removed.

5. A process as claimed in claim 3, wherein the liquids are removed separately after liquefaction of the crystal layers by heating.

6. A process as claimed in claim 1, wherein the cold surfaces used are flat or cylindrical surfaces.

7. A process as claimed in claim 1, wherein a liquid trickle film flows over, or liquid completely fills and flows through, flat or cylindrical cold surfaces.

8. The process of claim 7, wherein the flat or cylindrical cold surfaces are tubes.

* * * * *